United States Patent
Moore

(10) Patent No.: US 10,137,240 B2
(45) Date of Patent: Nov. 27, 2018

(54) CAPILLARY CHANNEL STRUCTURE FOR DISPENSE INTERFACE

(71) Applicant: Sanofi-Aventis Deutschland GmbH, Frankfurt am Main (DE)

(72) Inventor: David Moore, Leicestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 529 days.

(21) Appl. No.: 14/414,385

(22) PCT Filed: Jul. 10, 2013

(86) PCT No.: PCT/EP2013/064632
§ 371 (c)(1),
(2) Date: Jan. 12, 2015

(87) PCT Pub. No.: WO2014/009444
PCT Pub. Date: Jan. 16, 2014

(65) Prior Publication Data
US 2015/0196707 A1    Jul. 16, 2015

(30) Foreign Application Priority Data
Jul. 13, 2012 (EP) .................................... 12176405

(51) Int. Cl.
*A61M 5/14* (2006.01)
*A61M 5/19* (2006.01)
(Continued)

(52) U.S. Cl.
CPC .......... *A61M 5/141* (2013.01); *A61M 5/1408* (2013.01); *A61M 5/19* (2013.01);
(Continued)

(58) Field of Classification Search
CPC .... A61M 5/141; A61M 5/19; A61M 5/16827; A61M 5/345; A61M 5/1408
See application file for complete search history.

(56) References Cited

U.S. PATENT DOCUMENTS

| 533,575 A | 2/1895 | Wilkens |
| 4,109,653 A | 8/1978 | Kozam et al. |

(Continued)

FOREIGN PATENT DOCUMENTS

| CN | 1063467 A | 8/1992 |
| CN | 2401195 Y | 10/2000 |

(Continued)

OTHER PUBLICATIONS

English Translation of the Abstract of Chinese Patent Application No. 2401195 dated Oct. 24, 2017.

*Primary Examiner* — Nathan R Price
*Assistant Examiner* — Anh Bui
(74) *Attorney, Agent, or Firm* — McCarter & English, LLP

(57) ABSTRACT

The invention is related to a dispense interface for a drug delivery device for delivering at least two drug agents, comprising at least two two-ended flow regulation structures and a confluence, wherein each flow regulation structure comprises a fluid inlet opening at a first end, wherein each flow regulation structure comprises a fluid outlet opening connected to the confluence at a second end of the respective flow regulation structure and wherein at least one of the two-ended flow regulation structures comprises a capillary fluid channel. The invention is further related to a drug delivery device for delivering at least two drug agents comprising a dispense interface of the aforementioned kind, to a method for delivering at least two drug agents through an injection means of a drug delivery device and to a method (Continued)

for manufacturing a dispense interface of the aforementioned kind.

12 Claims, 13 Drawing Sheets

(51) Int. Cl.
*A61M 5/20* (2006.01)
*A61M 5/168* (2006.01)
*A61M 5/315* (2006.01)
*A61M 5/34* (2006.01)
*A61M 5/24* (2006.01)
*A61M 5/31* (2006.01)
*A61M 5/145* (2006.01)

(52) U.S. Cl.
CPC ............ *A61M 5/20* (2013.01); *A61M 5/1454* (2013.01); *A61M 5/16827* (2013.01); *A61M 5/31546* (2013.01); *A61M 5/345* (2013.01); *A61M 2005/2407* (2013.01); *A61M 2005/2496* (2013.01); *A61M 2005/3117* (2013.01); *A61M 2205/50* (2013.01)

(56) References Cited

U.S. PATENT DOCUMENTS

| | | |
|---|---|---|
| 5,078,699 A | 1/1992 | Haber et al. |
| 5,226,895 A | 7/1993 | Harris |
| 5,253,785 A | 10/1993 | Haber et al. |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,665,067 A | 9/1997 | Linder et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 8,074,843 B2 | 12/2011 | Keller |
| 8,142,402 B2 | 3/2012 | Sogaro |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2006/0206052 A1* | 9/2006 | Kriesel ............... A61M 5/1408 604/82 |
| 2007/0083155 A1 | 4/2007 | Muller |
| 2009/0275916 A1 | 11/2009 | Harms et al. |

FOREIGN PATENT DOCUMENTS

| | | |
|---|---|---|
| CN | 1721005 A | 1/2006 |
| CN | 101394937 A | 3/2009 |
| EP | 0669100 A1 | 2/1995 |
| EP | 0937471 A2 | 8/1999 |
| EP | 0937476 A2 | 8/1999 |
| EP | 2283885 A1 | 2/2011 |
| WO | 9210425 A1 | 6/1992 |
| WO | 9422507 A2 | 10/1994 |
| WO | 0938554 A1 | 8/1999 |
| WO | 0110484 A1 | 2/2001 |

* cited by examiner

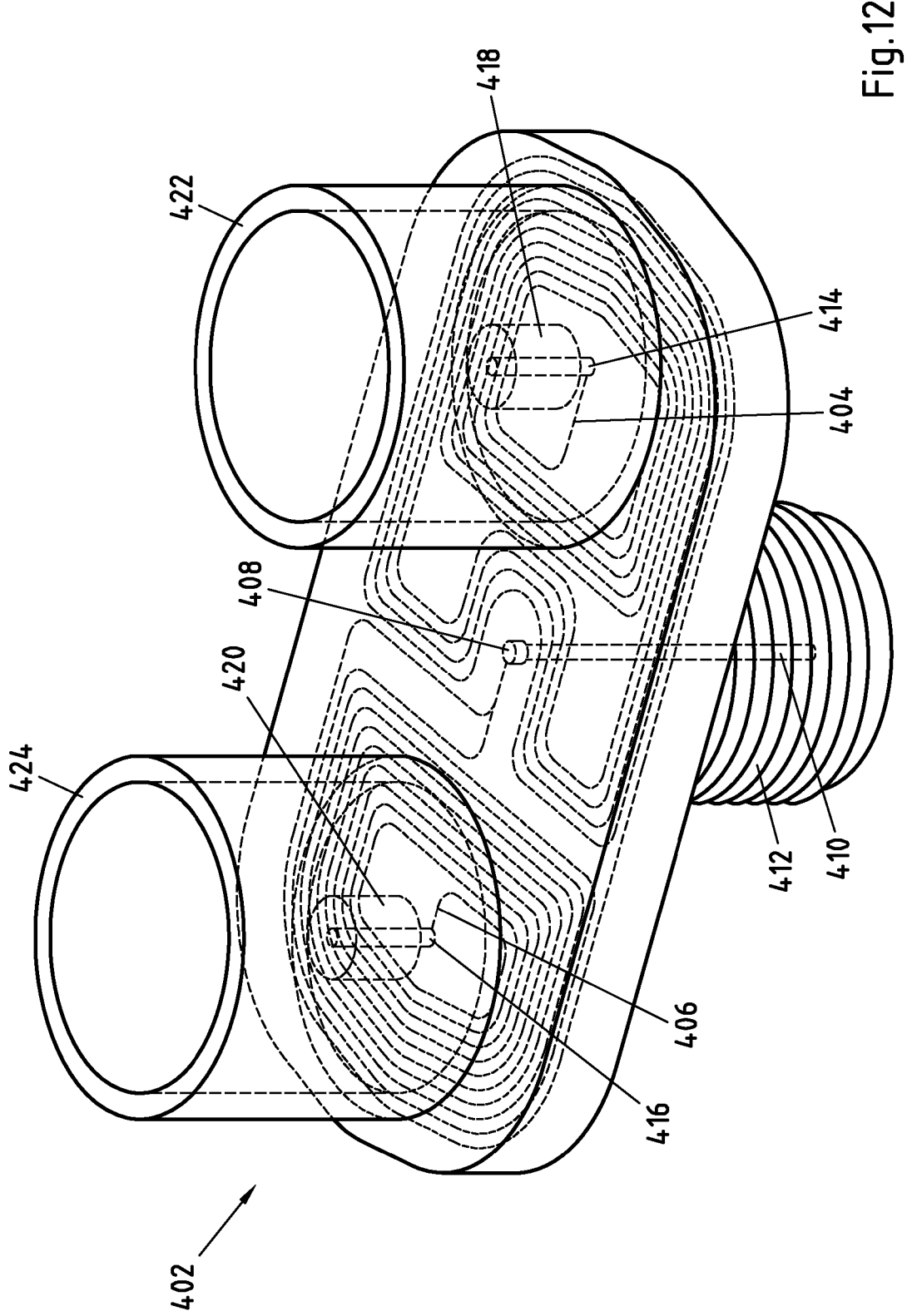

CAPILLARY CHANNEL STRUCTURE FOR DISPENSE INTERFACE

CROSS REFERENCE TO RELATED APPLICATIONS

The present application is a U.S. National Phase Application pursuant to 35 U.S.C. § 371 of International Application No. PCT/EP2013/064632 filed Jul. 10, 2013, which claims priority to European Patent Application No. 12176405.4 filed Jul. 6, 2012. The entire disclosure contents of these applications are herewith incorporated by reference into the present application.

FIELD OF INVENTION

The present patent application relates to a dispense interface for a drug delivery device for delivering at least two drug agents, to a drug delivery device for delivering at least two drug agents, to a method for delivering at least two drug agents, and to a method of manufacturing a dispense interface for a drug delivery device.

BACKGROUND

There are various medical devices for delivering at least two drug agents from separate reservoirs. Such drug agents may comprise a first and a second medicament. Such a medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

SUMMARY

In such a drug delivery device, a dispense interface is the part of the drug delivery device through which the drug agents to be delivered, which are fluids, pass from their respective reservoirs to a—usually shared—point from which they flow towards an outlet of the injector, for example through an injection needle. In order to provide this kind of functionality, the dispense interface enables a selective and controlled flow from each reservoir towards the injection needle. Each reservoir, of which in the present case there are at least two, may in particular be formed by a cartridge.

Certain disease states require treatment using one or more different medicaments. Some drug compounds need to be delivered in a specific relationship with each other in order to deliver the optimum therapeutic dose. The dispense interface described herein is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose, or alternatively these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be fitted with a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

In the context of the present invention, the drug delivery device comprises a dispense interface having a confluence through which the flow of medicaments from at least two cartridges passes—though not necessarily simultaneously. Thus, the medicaments from the at least two cartridges may share the same injection needle arranged downstream from that confluence.

For the controlled delivery of at least two medicaments from the cartridges corresponding to the reservoirs and containing the primary and secondary medicament, respectively, to the injection needle via the dispense interface, there needs to be a mechanism by which the fluid flow between the reservoirs and the confluence can be controlled.

One way of controlling the fluid flow is to use one or more pressure-operated valves, which may for example be implemented as diaphragm valves, also known as membrane valves. Valves of this type comprise a flexible membrane which is configured to change its shape between a closed state of the valve and an open state of the valve.

When there is no discharge of the respective medicament from its cartridge, there is little or no pressure across the corresponding diaphragm valve, and the valve is then in the closed state. In this closed state, the valve presents a physical barrier to the flow of fluid out from its cartridge and also acts to block any flow of fluid into the cartridge.

When the process of discharging a respective medicament from its cartridge begins, the medicament is pushed out of the cartridge, for example by a bung that advances into the cartridge. The pressure applied by the bung at the far end of the cartridge increases the pressure of the medicament across the corresponding diaphragm valve. At a predetermined level of pressure, the membrane changes its shape, which may comprise an inversion of its shape from concave to convex or vice versa, so that the valve changes from the closed state to the open state, and the fluid medicament is permitted to flow through the valve in the forward direction.

Besides preventing forward flow of the respective medicament from its cartridge to the needle at forward pressures below a predetermined threshold, the valves also serve the purpose of preventing back flow and contamination into each of the respective cartridges. This risk of backflow exists because medicaments from the at least two cartridges flow through a shared confluence as well as through a shared volume in the pathway to the injection needle. Thereby, there is in principle a flow path from one medicament cartridge to the other that includes the confluence.

Another factor contributing to the risks of such backflows is the occurrence of pressure drops generated during the discharge of a medicament. Such a pressure drop can in particular be developed by the injection needle itself, as such injection needles are of very small diameter and offer considerable resistance to flow. And because the bungs and the associated drive systems that build up the pressure in the cartridges may themselves be compliant (that is, will compress under increasing pressure) the pressure generated by the injection needle during the discharge of a first medicament can cause a backflow of the medicament towards or into the cartridge of another medicament.

This backflow is undesirable as it causes cross-contamination of the drugs or medicaments in the cartridges, and also may reduce the dose accuracy of the delivery device.

To prevent this from happening, when the pressure across the diaphragm valve increases in the reverse direction (back pressure), the valve should act to block any fluid flow (backflow) into the cartridge. However, conventional valves, and including membrane valves, involve moving or flexing parts, which are both challenging to manufacture as well as prone to malfunction. In the latter case the valve may not close tightly, thereby allowing backflow leakage past the valve.

In the case that the closing of the valve is imperfect, an undesired backflow of the respective other medicament into the cartridge may result. And while the use of a short length of channel between the cartridge and the valve, in combination with a small volume for the chamber of the valve provides an advantageous small dead volume of medicament during the injection process, these same features will also afford a short pathway for the backflow of medicament into the other cartridge and therefore make cross-contamination of drugs or medicaments into the other cartridge more likely.

Although even a small leakage backflow past the valve and into the other channel is undesirable, nevertheless if it does occur it may still be manageable provided that leaked medicament does not reach the other cartridge. However, backflow that allows leaked medicament to reach into the other cartridge should be prevented under all conditions in order to prevent cross-contamination of the drugs or medicaments within the cartridge.

Thus it is an object of the invention to provide a dispense interface for a drug delivery device for delivering at least two drug agents, a drug delivery device for delivering at least two drug agents, and a method for delivering at least two drug agents with an alternative mechanism for controlling the fluid flow through the dispense interface. It is further an object of the invention to provide a method for manufacturing such a dispense interface for a drug delivery device.

With regard to the dispense interface, this object is solved by a dispense interface for a drug delivery device for delivering at least two drug agents, comprising at least two two-ended flow regulation structures and a confluence, wherein each flow regulation structure comprises a fluid inlet opening at a first end, wherein each flow regulation structure comprises a fluid outlet opening connected to the confluence at a second end of the respective flow regulation structure, and wherein at least one of the two-ended flow regulation structures comprises a capillary fluid channel.

By using capillary fluid channels as means for regulating flow through the dispense interface instead of using valves, there is no need for including a valve structure that is distinct from the channel structure through which the medicaments flow for injection. Essentially, all that is required is a narrow fluid channel (capillary) and an adequate minimum length of that capillary channel.

By adopting a channel geometry arranged into a capillary form, the cross-sectional area of the channel over which diffusion mixing of the medicaments can occur is reduced. Also, by providing a capillary of considerable length, the diffusion concentration gradient of the medicaments, and therefore the rate of diffusion of the medicaments, is reduced.

If such a structure is left alone without external disturbance, the diffusion time, which can be determined by methods including random walk model simulation, is in the order of months or years, and this affords a fluid segregation equivalent to that of a conventional valve. This fluid segregation works in both directions, both into and out of the cartridges.

As well as the mechanism of diffusion, a further mechanism by which mixing can occur at a fluid interface is by the action of convection currents. These convection currents may be set up by local density gradients caused by the different densities of the medicaments. Advantageously, these effects are reduced or even eliminated by reducing the width of the fluid envelope. The use of a capillary form therefore reduces the effect of such convection currents, and, depending upon the value of the Rayleigh Number of the fluid within the capillary, may even eliminate convection effects entirely.

Therefore, both by reduction of the diffusion rate and by the reduction or elimination of convection effects, in the absence of external disturbance the capillary structure forms a barrier to the mass transfer of medicament and provides fluid segregation that prevents mixing of the medicaments and cross-contamination of the cartridges.

Further, the structural layout of the dispense interface associated with the volume of the capillary fluid channels according to the invention may be used to provide a barrier to the backflow caused by the disturbing pressures generated by the discharge of medicaments.

Besides offering the possibility of solving the problem of backflow with a specific physical structure associated with the volume of the dispense interface, the present invention also solves the problem of backflow with a solution specifying a method.

As a further advantage, such a dispense interface may at least partially obviate the need for moving parts, which means that there is no risk of jamming or valve leakage. Moreover, dose accuracy may be improved. The reason for this is that the opening and closing behavior of valves, including membrane valves as a function of the pressure applied can be hard to predict. The flow properties of a capillary fluid channel may be more predictable, therefore the dose administered as a function of the pressure applied can be regulated more accurately.

As a yet further advantage, also other problems associated with the use of valves can be avoided. Because the valves need to provide a sealed physical barrier to flow, often silicone or other rubber-like material is used for the valves. However, silicone may be active in removing material from fluids, and other rubber-like materials may also be active with the medicament, i.e. may chemically react with it in some way. The use of capillary fluid channels makes the use of such material unnecessary.

With regard to the method for delivering at least two drug agents, the object of the invention is solved by a method for delivering at least two drug agents through an injection means of a drug delivery device, wherein the drug delivery device comprises a reservoir for each drug agent comprising the respective drug agent in fluid form, means for applying pressure to the respective drug agent comprised in each reservoir, an injection means for injecting the drug agents, and a fluid connection arrangement configured to fluidly connect each reservoir to the injection means, the method comprising pressing a first drug agent comprised in a first reservoir into the fluid connection arrangement by applying a first pressure to the first drug agent comprised in the first reservoir, and pressing a second drug agent comprised in a second reservoir into the fluid connection arrangement by applying a second pressure to the second drug agent comprised in the second reservoir.

This approach is particularly suitable when a simultaneous injection of all medicaments is acceptable. Then, preferably, the method for delivering the at least two drug agents is that they are dispensed simultaneously out of their reservoirs and through their fluid paths all the way to the confluence, i.e. to the point where the fluid paths of the at least two drug agents meet and the drug agents converge, and still further to the injection needle. And preferably, when there is simultaneous delivery of the medicaments, the pressures of each of the drug agents in each of the reservoirs are made substantially equal to each other.

Since the pressure applied to each drug agent in its respective reservoir is substantially equal, also the respective hydrostatic pressures of the respective drug agents at their respective regions of contact in the fluid path to the injection needle are substantially equal. Thereby, the hydrostatic pressure of each fluid agent substantially prevents back flow of the other drug agents from the present positions of the regions of contact in a direction towards or even reaching into the respective reservoir. This means that while one of the drug agents may have a temporarily or slightly higher pressure and therefore may cause some backflow from the present region of contact up the respective other fluid paths, such a pressure imbalance is only temporary or small and in any case insufficient to cause a backflow all the way to another reservoir. Thereby backflow can be avoided without having to endow a capillary fluid channel with enough volume to contain any potential backflow in its entirety.

In the following, the terms used to describe the invention shall be further explained. A flow regulation structure is any entity through which fluid can flow and which may act to block the fluid or may act to permit the flow of fluid. The flow regulation structure is two-ended in that it has a fluid inlet opening and fluid outlet opening.

There are at least two flow regulation structures in the dispense interface. The fluid inlet opening of each flow regulation structure is physically distinct from the fluid inlet opening of the other flow regulation structures and is configured to permit fluid flow into the respective flow regulation structure at a first end of the respective flow regulation structure. However, while each flow regulation structure has its own fluid outlet opening, the fluid outlet openings of at least two of the flow regulation structures meet at a common point or cavity which is the confluence. Thus, each fluid outlet opening is configured to permit fluid flow from the respective flow regulation structure into the confluence at the second end of the respective flow regulation structure.

A capillary fluid channel is a fluid channel in which the ratio of length of the fluid channel versus width of the fluid channel is such that the capillary effect already described with regard to the barrier to mass transport arises in the fluid channel. In particular, the dimensions of the fluid channel may be such that the capillary effect already described arises for a fluid consisting of water, of insulin glargine or of a GLP-1 fluid.

An injection means may be any apparatus for injecting fluid. In particular, the injection means may comprise an injection needle. The injection means is shared by the drug agents of at least two reservoirs.

A reservoir may be any volume configured to enclose a fluid, in particular a drug agent, for storage. In particular, a cartridge for a drug delivery device may present such a reservoir.

The means for applying pressure may comprise any apparatus that is configured to apply pressure to a fluid, in the present case a drug agent, contained in a reservoir. In particular, the means for applying pressure may be configured to mechanically compress the interior volume of a reservoir, thereby pressing the drug agent contained in the reservoir out of the reservoir.

A fluid connection arrangement may present any structure that provides fluid connections or fluid channels from each reservoir of the drug delivery device to the injection means. In particular, the fluid connection arrangement may comprise a dispense interface for a drug delivery device according to the invention, wherein each fluid inlet opening is fluidly connected to a respective reservoir and the fluid outlet opening is fluidly connected to the injection means.

The observation that the first drug agent and the second drug agent converge means that the respective drug agents come into contact at a contact region or area. This may or may not involve a mixing of the first drug agent and the second drug agent. The contact region may therefore be a phase surface between the first drug agent and the second drug agent. However, the contact region may equally be a larger volume in which the first drug agent and the second drug agent mix.

Further the observation that the first pressure is substantially equal to the second pressure means that during delivery of the at least two drug agents through the injection means there is an equilibrium between the first drug agent and the second drug agent such that the contact region between them remains largely stationary, even though both drug agents are delivered through the injection means. In any case, while there may be a slight displacement of the contact region by a temporary or small excess hydrostatic pressure of one of the drug agents, the position of the contact region remains at the confluence or within the lengths of the capillary fluid channels.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

In a preferred embodiment of the dispense interface, each of the at least two two-ended flow regulation structures comprises a capillary fluid channel. This way valves with moving or flexing components can be avoided.

In a further preferred embodiment of the dispense interface, each capillary fluid channel has a volume configured to contain a backflow from a respective other of the flow regulation structures. In other words, each capillary fluid channel is dimensioned such that, if a backflow of a drug agent from one of the other flow regulation structures occurs, the backflowing drug agent is fully contained within the capillary fluid channel and does not flow back all the way to the fluid inlet opening of the capillary fluid channel.

The according dimensioning of the capillary fluid channel depends on a variety of factors. In particular, the volume of the capillary fluid channel may depend on the hydraulic volumetric compliance of the cartridges, the pressure developed by the fluid, i.e. the drug agent, to be contained during its dispense, the resistance to flow offered by the fluid channels and the characteristics of injection needle, the dispense rate of the fluid to be contained, i.e. the drug agent associated with the flow path of the respective other flow regulation structure, the quantities of the drug agents that are to be dispensed by the device and how the ratio of these quantities may need to be varied, and also the dispense method, which may be either consecutive or simultaneous, or a combination of the two.

For example, a first capillary fluid channel may be configured for dispensing insulin glargine and have a volume of 50 microliters. A second capillary fluid channel may be configured for dispensing a GLP-1 fluid and have a volume of 30 microliters. In this example the geometries of the two capillary fluid channels may be adjusted to accommodate the required physical properties of the fluid channels, which depend upon the compliances of the two cartridges, the dispense method, the dispensed quantities that the device must provide as well as the properties of the respective fluid to be channeled through the fluid channel. Such properties of the respective fluids may include the viscosities and densities of the fluids.

Relying on the ability of the capillary fluid channel to absorb this volume of backflowing drug agent is particularly suitable when there is a consecutive injection of the drug agents, because in that case the pressure of the drug agents to be injected is higher than the pressure of the other medicaments.

In another preferred embodiment of the dispense interface, at least one of the two-ended flow regulation structures comprises a valve. Thereby the use of a capillary fluid channel for regulating the flow from a first cartridge is combined with the use of a conventional valve for regulating the flow from a second cartridge. This may be advisable when a conventional valve is suitable for at least one of the medicaments. For example, if the primary medicament must be dosed very precisely but the accuracy of the dosage of the secondary medicament is less critical, then the effect of the variable opening and closing pressures of the valve upon the dispensed quantity of the second medicament is less important. Or, for another example, if some contamination of the second medicament by the first medicament is permitted, then some leakage of the valve is less important. In such cases, the most economical trade-off may consist of having a conventional valve for one medicament and a capillary structure for the other medicament.

In yet another preferred embodiment of the dispense interface, at least one of the two-ended flow regulation structures comprises a sequential arrangement of a valve and a capillary fluid channel. In such a sequential arrangement, either the valve is arranged downstream of the capillary fluid channel or the capillary fluid channel is arranged downstream of the valve, with the former arrangement being especially preferred. In a combined arrangement of a valve and a capillary fluid channel, one may achieve the benefits of having a capillary fluid channel even with a reduced length of the capillary fluid channel and the resultant reduced volume of the capillary fluid channel. And although the valve is susceptible to leakage in the intervals between the dispense events, the capillary structure acts to block mass transport of medicaments during these intervals.

In still another preferred embodiment of the dispense interface, each capillary fluid channel has a channel width of approximately 0.3 mm or 0.4 mm. In a capillary fluid channel of circular cross section, the width of the capillary fluid channel corresponds to the diameter of the capillary fluid channel. Such a diameter of the capillary fluid channel provides sufficient volume for containing potential backflow from the respective other flow regulation structures without the need for a very great length of capillary, and also moderates the pressure needed to deliver the medicament through the capillary fluid channel while ensuring a sufficiently high throughput of medicament. The capillary fluid channel may advantageously have a rounded or circular cross-section.

In a preferred embodiment of the dispense interface, each capillary fluid channel has a channel length of approximately 50 cm, thus providing a capillary volume of 35 microliters at a capillary diameter of 0.3 mm.

In another preferred embodiment of the dispense interface, each capillary fluid channel is arranged to form a planar meandering pattern. Arranging the capillary fluid channel on a common plane allows a convenient manufacture of the dispense interface. Arranging each capillary fluid channel to form a meandering pattern permits the channel length of the capillary fluid channel to be maximised while at the same time minimizing the planar area required to form the capillary fluid channel.

In yet another preferred embodiment of the dispense interface, the planar meandering pattern consists of straight sections and rounded sections. Since only straight or rounded sections make up the capillary fluid channel, the capillary fluid channel does not comprise sharp radii or abrupt changes of direction. Thereby the fluidic properties of the capillary fluid channel promote laminar flow within the channels, and minimise radial mixing within the capillary channels due to induced turbulence.

In a still further preferred embodiment of the dispense interface, the confluence is configured to permit flow to a holding chamber of the dispense interface. Since the holding chamber is arranged downstream from the confluence, the fluid from all cartridges is arranged to pass through the holding chamber.

In a further preferred embodiment of the dispense interface, the holding chamber terminates at an outlet port at a distal end of the dispense interface.

In a preferred embodiment of the dispense interface, the dispense interface comprises a respective stub around each fluid inlet opening at a proximal end of the dispense interface, wherein each stub is configured to receive a respective fluid cartridge. Each stub serves to position its associated fluid cartridge such that the fluid outlet of the cartridge is properly aligned with the associated fluid inlet opening of the dispense interface.

In another preferred embodiment of the dispense interface, the dispense interface is made of polyolefin. In particular, the dispense interface may be made of cyclopolyolefin, which is a rigid polymer that has good properties with medicaments and cresol. Thereby, despite the capillary fluid channels requiring a large surface area to volume ratio, a good biocompatibility is nevertheless achieved. Moreover, the use of elastomeric, rubberlike elements such as silicone avoided. With regard to the ratio of surface area to volume, a channel width of 0.3 mm is preferred over smaller channel widths.

In yet another preferred embodiment of the dispense interface, the dispense interface comprises at least two integral parts, wherein a first integral part comprises a proximal end of the dispense interface and wherein a second integral part comprises a distal end of the dispense interface. Thereby the dispense interface can be assembled by the combination of the first and second integral part, for example by laser welding, ultrasonic welding, adhesive bonding, and/or the like.

In a further preferred embodiment of the dispense interface, the first integral part comprises a first boundary surface of each capillary fluid channel and the second integral part comprises a second boundary surface of each capillary fluid channel. In other words, each capillary fluid channel is formed at the boundary encompassed by the first integral part and the second integral part. If the wall of each capillary fluid channel is divided into a lower portion and an upper portion, then the lower portion wall is formed by one of the first or second integral part and the upper portion is formed by the respective other of the first or second integral part. Thereby no narrow but lengthy cavity needs to be formed in either of the integral parts. Consequently, production of the dispense interface is facilitated.

In a still further preferred embodiment of the dispense interface, each capillary fluid channel is formed by joining of the first integral part and the second integral part.

With regard to the drug delivery device, the object of the invention is further solved by a drug delivery device for delivering at least two drug agents comprising a dispense interface according to the invention. Preferred embodiments of the drug delivery device correspond to drug delivery devices which comprise preferred embodiments of the dispense interface as described.

In a preferred embodiment of the method for delivering at least two drug agents, applying a first pressure to the first drug agent comprised in the first reservoir and applying a second pressure to the second drug agent comprised in the second reservoir occurs simultaneously. If the first and the second pressure are substantially equal, this ensures substantially equal hydrostatic pressure between the first drug agent and the second drug agent. The pressures in the first reservoir and in the second reservoir may both be maintained at a substantially constant value during the period of the dispense. Alternatively, the pressures in the first reservoir and the second reservoir may instead both be varied during the period of the dispense, provided that the two pressures are kept substantially equal to each other.

This method for delivering at least two drug agents may also be adapted to accommodate, for example, those circumstances where a large quantity of the first medicament is required in combination with only a small quantity of the second medicament, and also where these quantities might be reversed on a day-to-day basis, such as might arise according to the varying clinical needs of the user.

By way of example, a first pressure is applied to the first drug agent comprised in the first reservoir, and a second pressure is simultaneously applied to the second drug agent comprised in the second reservoir, where the first and second pressures are substantially equal. But in this method, to accommodate the needs of the user, the volume of drug agent that is delivered from the first reservoir is much smaller than the volume delivered from the second reservoir.

By way of further example, the deliveries from the first and second reservoirs might at first be substantially equal during a first interval that the pressures in the first and second reservoirs are also substantially equal and rise progressively towards a steady-state value. Then the delivery from the first reservoir might be reduced or even stopped but delivery from the second reservoir continued until the correct combined dosing is achieved. Advantage may be gained by varying the delivery rate from the second reservoir in concert with the reduction in the delivery from the first reservoir, as may be determined by hydraulic flow considerations by those skilled in the art.

In another preferred embodiment of the method for delivering at least two drug agents, applying a first pressure to the first drug agent comprised in the first reservoir and applying a second pressure to the second drug agent comprised in the second reservoir occurs alternatingly in intervals. This means that at any point in time either the first pressure is applied to the first drug agent comprised in the first reservoir or the second pressure is applied to the second drug agent comprised in the second reservoir. This may also be described as an interleaved application of pressure on the drug agents in their respective reservoir. During the application of pressure on one of the drug agents, the equilibrium of hydrostatic pressure at the contact region of the drug agents is temporarily disturbed. However, by the resulting small displacement of the contact region and a choice of sufficiently small intervals for alternating the pressure application, these disturbances remain temporary and insubstantial.

In a further preferred embodiment of the method for delivering at least two drug agents, the means for applying pressure comprise a bung for each reservoir, wherein the bung is arranged within the respective reservoir and configured to apply pressure onto the drug agent within the reservoir. This preferred embodiment of the method for delivering at least two drug agents may also be alternatively or in addition be characterized in that applying a first pressure to the first drug agent comprises advancing a first bung in the first reservoir and that applying a second pressure to the second drug agent comprises advancing a second bung in the second reservoir.

When the pressure on each drug agent in its respective reservoir is to be applied in parallel, the bung for each reservoir likewise advances in parallel. Conversely, when the pressure on each drug agent in its respective reservoir is to be applied in an interleaved way and thereby alternatingly, also the bung for each reservoir advances alternatingly.

In a yet further preferred embodiment of the method for delivering at least two drug agents, the first bung is advanced at a first rate and the second bung is advanced at a second rate, wherein the ratio of the first rate to the second rate is based on the compliance of the first bung and the compliance of the second bung.

In order to minimize the containment volume of the capillaries, and to cope with blocked needles, the bungs can be advanced initially at a rate that corresponds to the cartridge compliances, so that approximately equal pressures are developed in the two cartridges. Then the advancement of one of the cartridges may be reduced or stopped, but continued with the other, in order to achieve different dose ratios.

In a preferred embodiment of the method for delivering at least two drug agents, the fluid connection arrangement comprises a confluence in fluid connection with the injection means, and a flow path for each drug agent fluidly connecting the respective reservoir comprising the respective drug agent to the confluence. The confluence in the context of this preferred embodiment may comprise or be identical to the confluence of the dispense interface according to the invention. Likewise, the flow path for each drug agent may comprise or be identical to the corresponding two-ended flow regulation structure of the dispense interface according to the invention.

In a further preferred embodiment of the method for delivering at least two drug agents, the first drug agent and the second drug agent converge in an area within the confluence.

In a yet further preferred embodiment of the method for delivering at least two drug agents, the first drug agent and the second drug agent converge in an area within one of the flow paths.

Further preferred embodiments of the method for delivering at least two drug agents correspond to methods for delivering at least two drug agents wherein the drug delivery device is a preferred embodiment of the drug delivery device as described.

For the preferred embodiment of the method for delivering at least two drug agents wherein for the drug delivery device at least one of the two-ended flow regulation structures comprises a sequential arrangement of a valve and a capillary fluid channel, there is a particularly advantageous technical effect to prevent backflow, as described in the following.

When, during its discharge, a drug agent is pressed through a flow regulation structure which is distinct from the flow regulation structure with the sequential arrangement of a valve and a capillary fluid channel, the pressure of that drug agent acts in the closing direction of the sequentially arranged valve. Especially in the case of a diaphragm valve, this causes the valve to slam shut and to thereby prevent backflow of the drug agent being discharged through the valve. Even when, after discharge of the drug agent, there is less or no pressure acting to tightly close the valve or if the valve leaks for some other reason, e.g. because of slight defects, the sequentially arranged capillary fluid channel prevents any traces of the drug agent that may have passed the valve in the reverse direction from diffusing all the way to the reservoir. Given the fact that, generally, twenty-four hours is the approximate interval between injections from each reservoir, this time is insufficient for a diffusion that traverses the entirety of the capillary fluid channel.

With regard to the method for manufacturing a dispense interface, the object of the invention is still further solved by a method of manufacturing a dispense interface for a drug delivery device according to the invention, which method comprises forming each of the at least two integral parts by moulding.

In a preferred embodiment of the method for manufacturing a dispense interface, the method comprises joining the at least two integral parts by ultrasonic welding.

In a further preferred embodiment of the method for manufacturing a dispense interface, the method comprises joining the at least two integral parts by adhesive bonding.

In a yet further preferred embodiment of the method for manufacturing a dispense interface, the method comprises connecting capillary tubing at its first end to a fluid inlet and at its second to the confluence.

Further preferred embodiments of the method for manufacturing a dispense interface correspond to methods for manufacturing preferred embodiments of the dispense interface as described.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which:

FIG. 12 illustrates a transparent perspective view of an exemplary dispense interface according to the invention;

DETAILED DESCRIPTION

Figure 1:
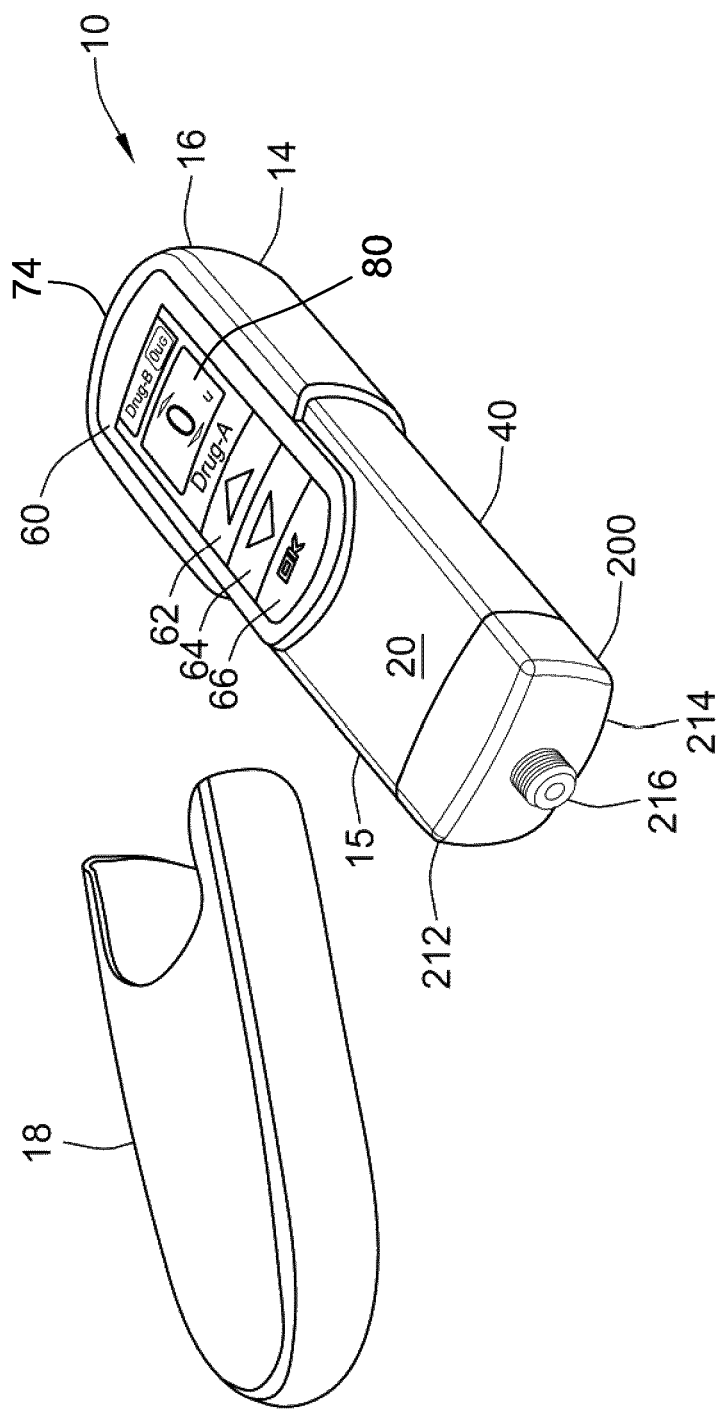
FIG. 1 illustrates a perspective view of a delivery device with an end cap of the device removed.
Figure 2:
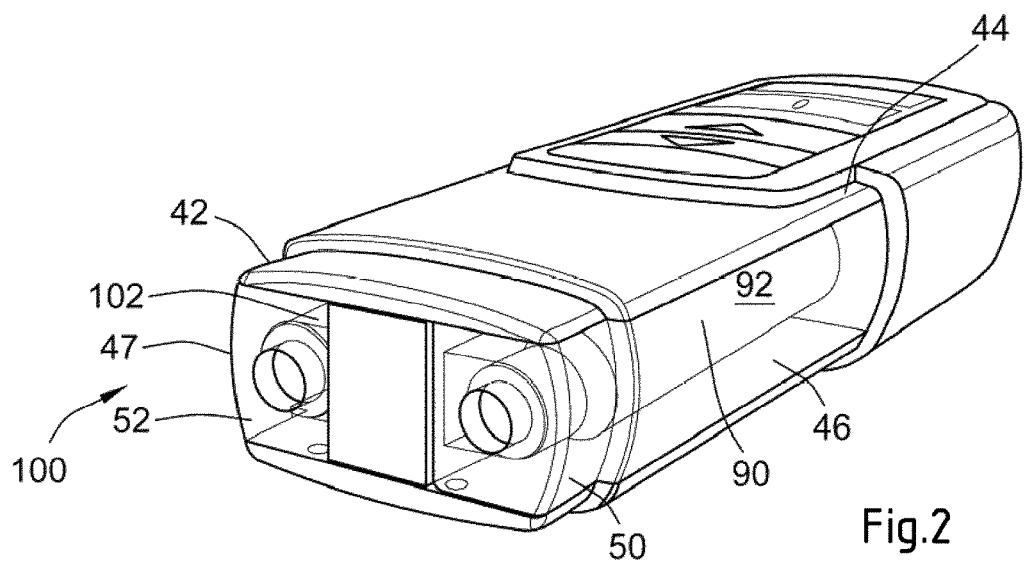
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. In one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user with certain device information, preferably information relating to the medicaments contained within the cartridge holder 40. For example, the user is provided with certain information relating to both the primary medicament and the secondary medicament.

Figure 3:
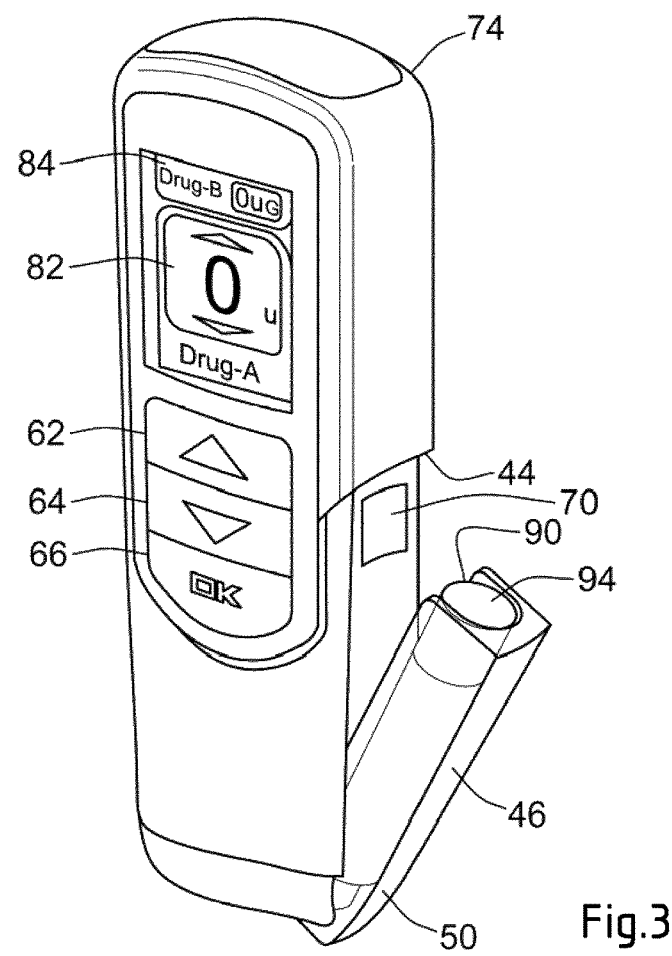
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
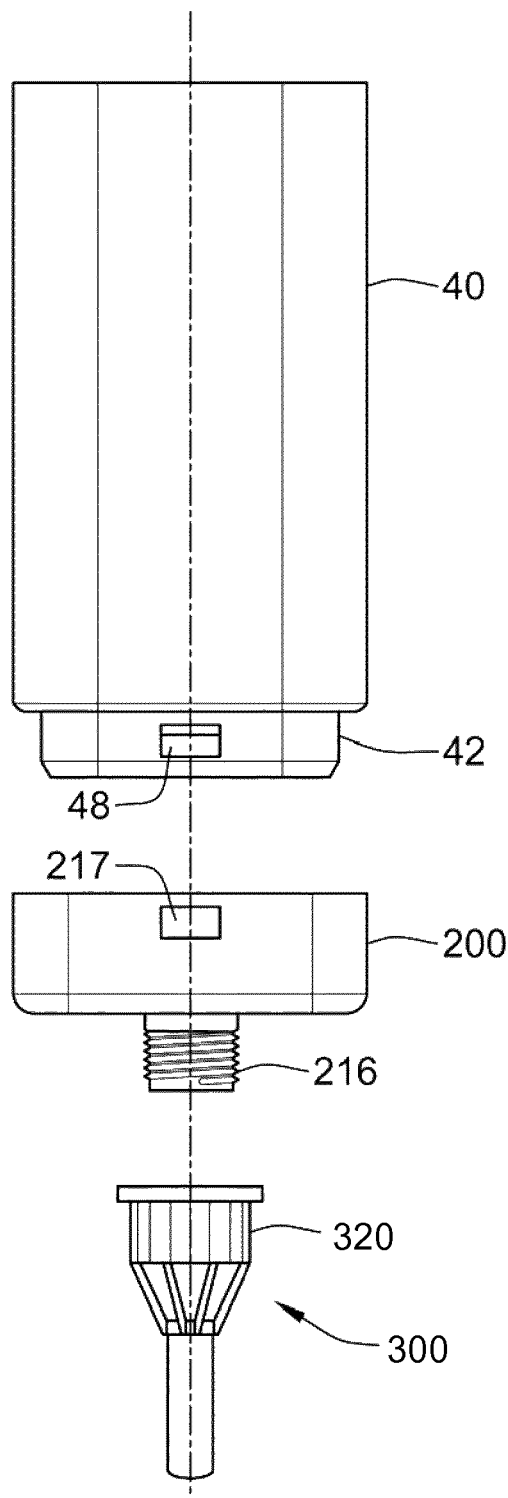
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly 300 that may be used with the interface 200 is also illustrated and is provided in a protective outer cap 320.

Figure 5:
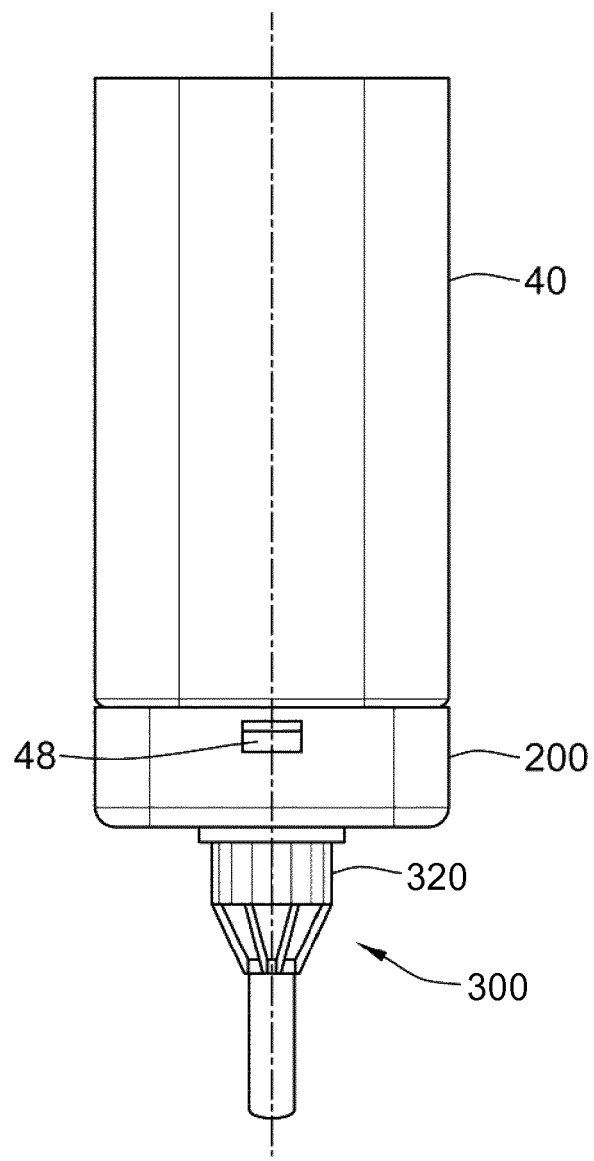
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
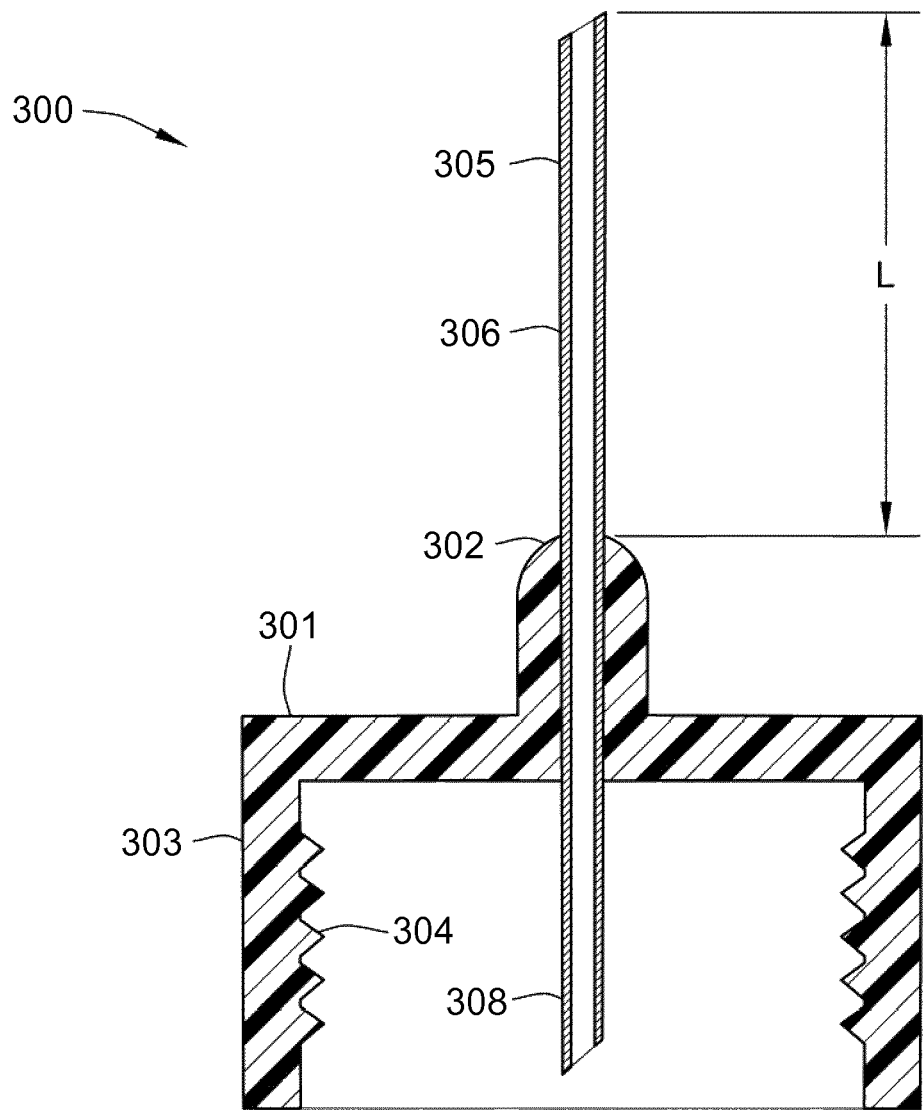
FIG. 6 illustrates one arrangement of a needle assembly that may be mounted on a distal end of the delivery device.
Figure 7:
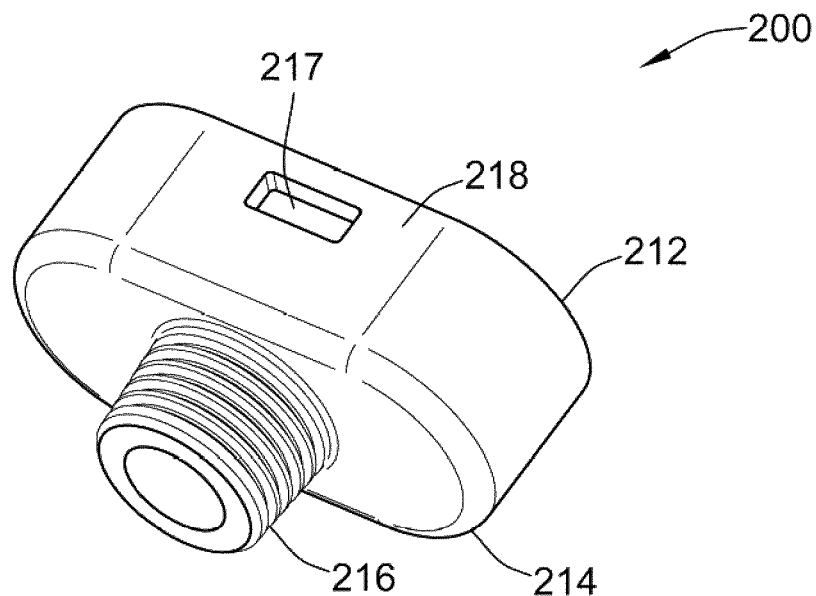
FIG. 7 illustrates a perspective view of the dispense interface illustrated in FIG. 4.

FIG. 5 also illustrates the needle assembly 300 and protective cover 320 coupled to the distal end of the dispense interface 200 that may be screwed onto the needle hub of the interface 200. FIG. 6 illustrates a cross sectional view of the double ended needle assembly 300 mounted on the dispense interface 200 in FIG. 5.

The needle assembly 300 illustrated in FIG. 6 comprises a double ended needle 306 and a hub 301. The double ended needle or cannula 306 is fixedly mounted in a needle hub 301. This needle hub 301 comprises a circular disk shaped element and a sleeve 303. Along an inner wall of this sleeve 303, a thread 304 is provided. This thread 304 allows the needle hub 301 to be screwed onto the dispense interface 200 which, in one preferred arrangement, is provided with a corresponding outer thread along a distal hub. At a center portion of the hub element 301 there is provided a protrusion 302. This protrusion 302 projects from the hub in an opposite direction of the sleeve member. A double ended needle 306 is mounted centrally through the protrusion 302 and the needle hub 301. This double ended needle 306 is mounted such that a first or distal piercing end 305 of the double ended needle forms an injecting part for piercing an injection site (e.g., the skin of a user).

Similarly, a second or proximal piercing end 308 of the needle assembly 300 protrudes from an opposite side of the circular disc so that it is concentrically surrounded by the sleeve 303. In one needle assembly arrangement, the second or proximal piercing end 308 may be shorter than the sleeve 303 so that this sleeve to some extent protects the pointed end of the back sleeve. The needle cover cap 320 illustrated in FIGS. 4 and 5 provides a form fit around the outer surface 303 of the hub 301.

Referring now to FIGS. 4 to 11, one arrangement of this interface 200 comprising a conventional valve seal 260 will now be discussed. In this one arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

After having thus explained the dispense interface 200 with a conventional valve seal 260, a dispense interface according to the invention comprising a flow regulation structure with capillary fluid channels will then be described with reference to FIG. 12 and FIG. 14 to FIG. 16. The discussion of the dispense interface with the conventional valve seal of FIG. 4 to FIG. 11 thereby provides the context for showing the principal functionality of the dispense interface according to the invention and its relation to the larger drug delivery device for which it is configured.

Returning to FIG. 4 to FIG. 11, the main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 300 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIGS. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
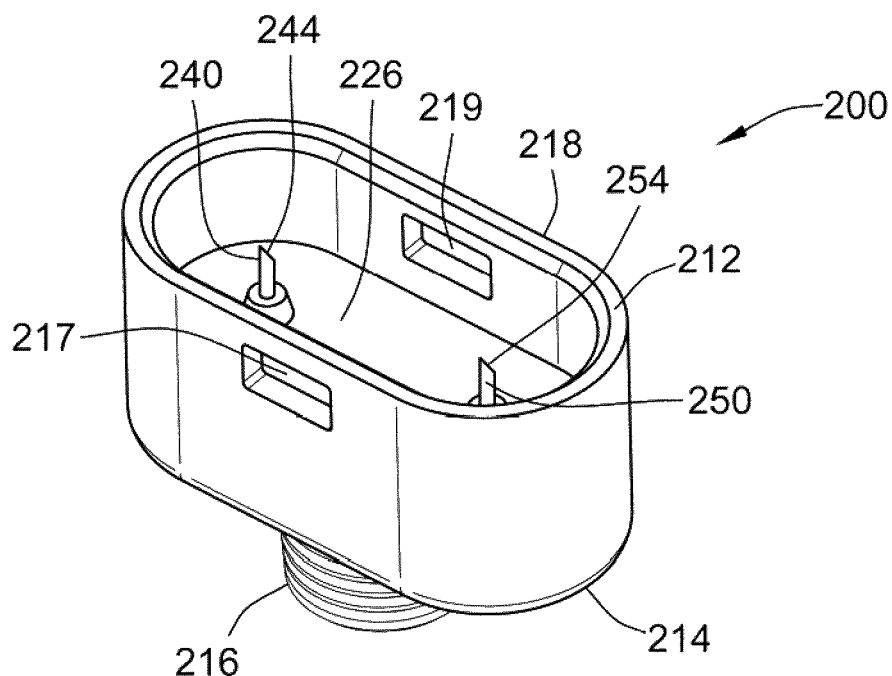
FIG. 8 illustrates another perspective view of the dispense interface illustrated in FIG. 4.
Figure 9:
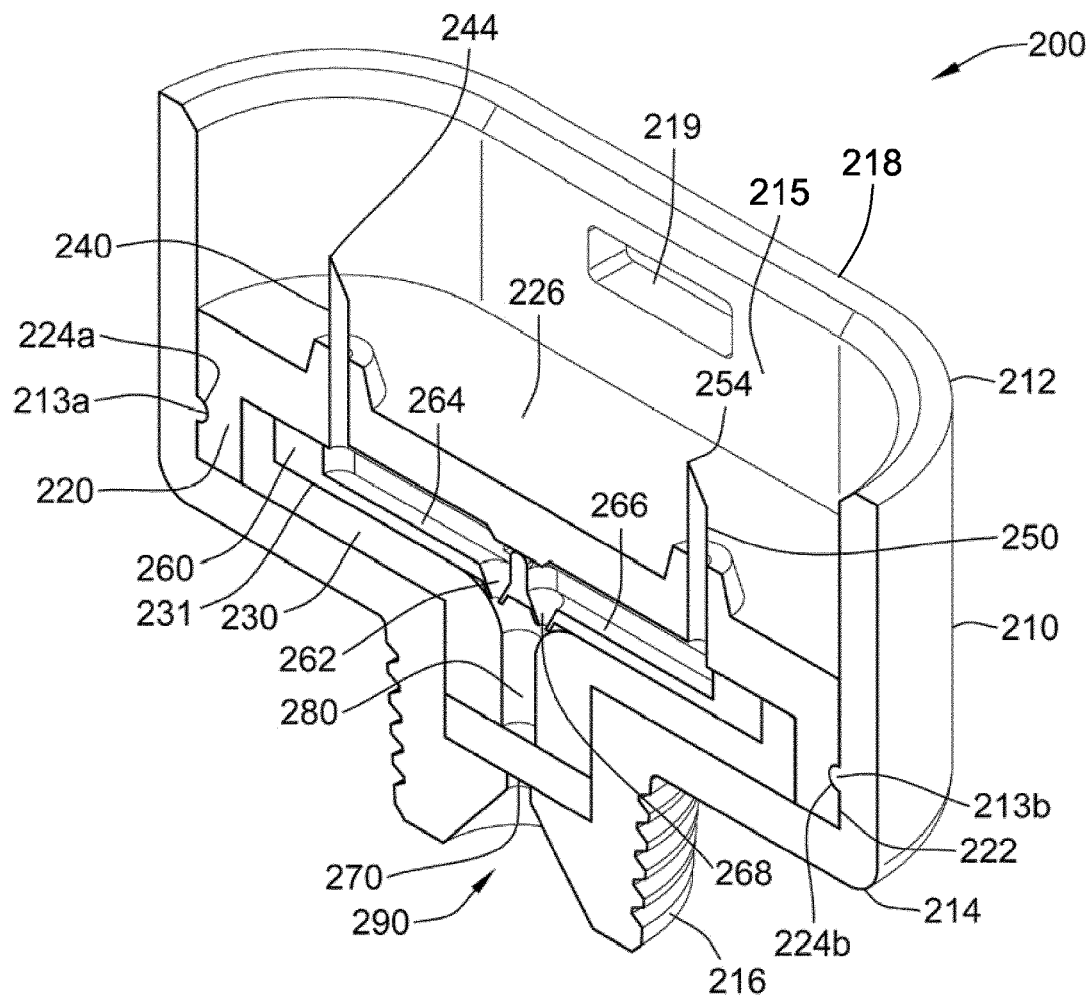
FIG. 9 illustrates a cross-sectional view of the dispense interface illustrated in FIG. 4 with a conventional seal valve.
Figure 10:
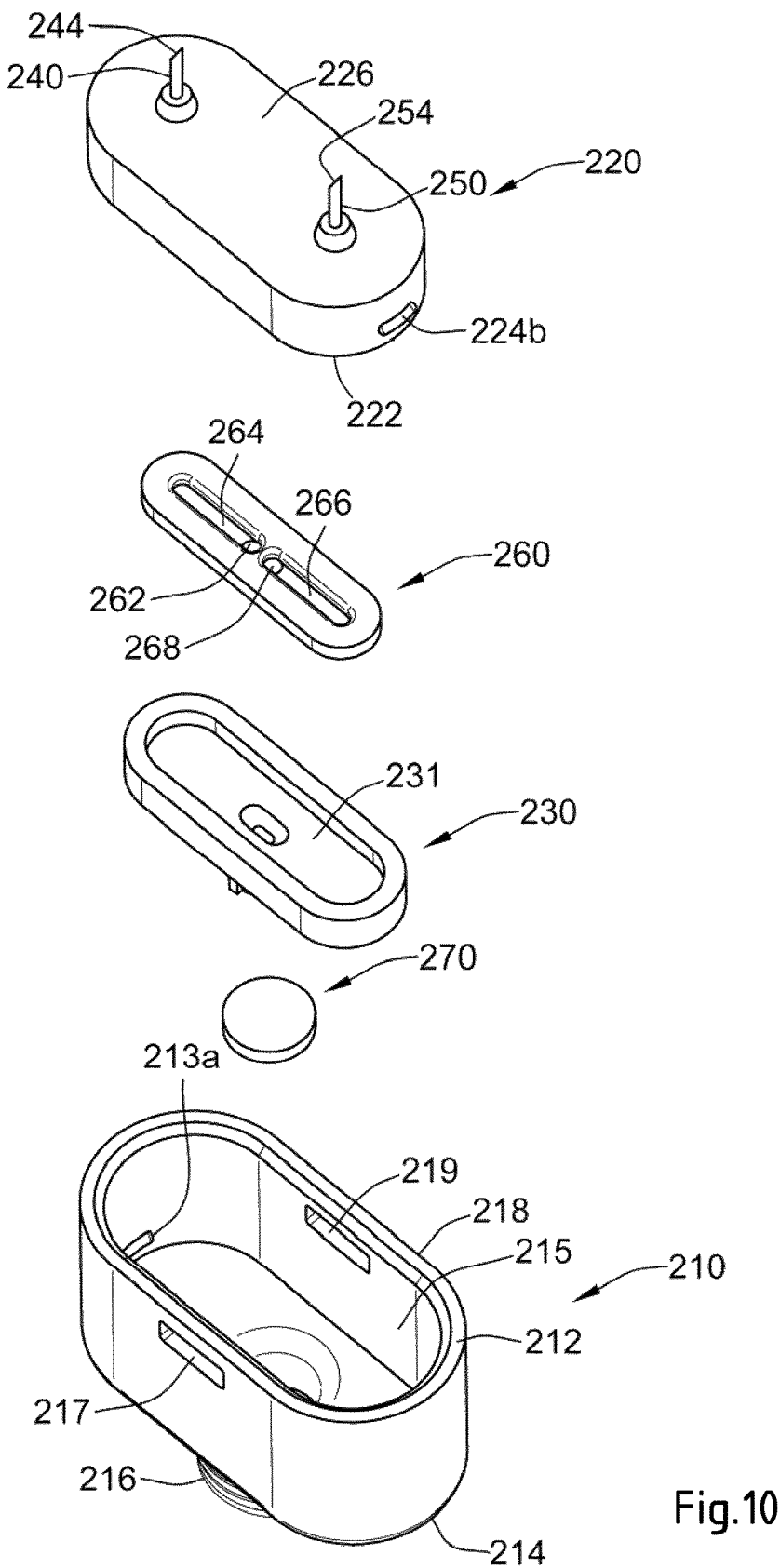
FIG. 10 illustrates an exploded view of the dispense interface illustrated in FIG. 4 with a conventional seal valve.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Figure 11:
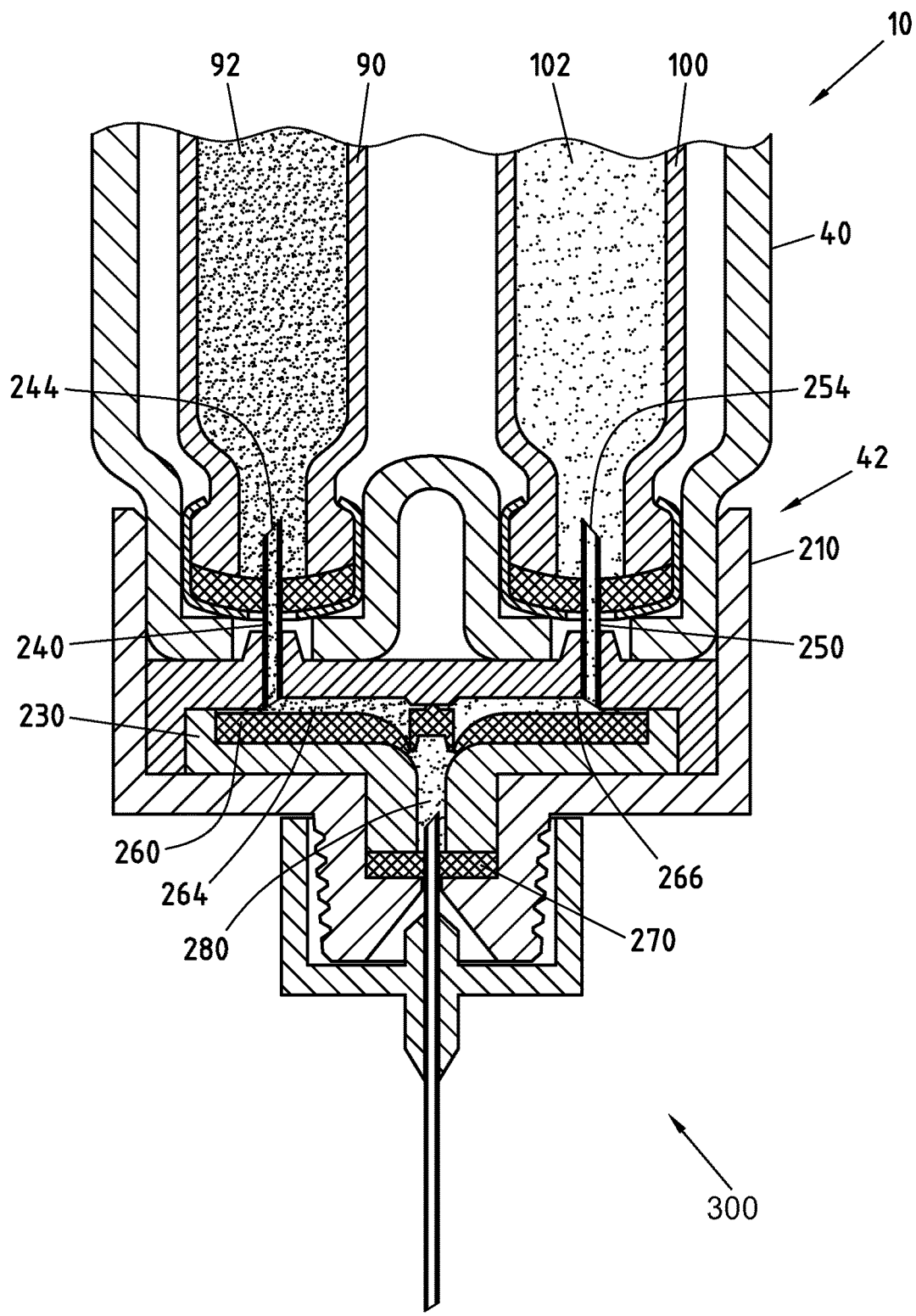
FIG. 11 illustrates a cross-sectional view of the dispense interface and needle assembly mounted onto a drug delivery device, such as the device illustrated in FIG. 1 and comprising a conventional seal valve.

As illustrated in FIG. 9 to FIG. 11, this dispense interface 200 further comprises a conventional valve arrangement. Such a valve arrangement could be constructed so as to prevent cross contamination of the first and second medicaments contained in the first and second reservoirs, respectively. This conventional valve arrangement may also be configured so as to prevent back flow and cross contamination of the first and second medicaments.

In particular, the dispense interface 200 illustrated in FIG. 9 to FIG. 11 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. This seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal 260.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

FIG. 11 illustrates the dispense interface 200 after it has been mounted onto the distal end 42 of the cartridge holder 40 of the drug delivery device 10 illustrated in FIG. 1. A double ended needle assembly 300 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates an arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 300. As illustrated, the proximal end of the double ended needle assembly is in fluid communication with the chamber 280.

In one arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

With reference to FIG. 12, there is illustrated a dispense interface 402 according to the invention for a drug delivery device as illustrated in FIG. 1. This preferred dispense interface is an alternative to the dispense interface 200 illustrated in FIG. 9 and implements a different mechanism to the same purpose, as shall be described in the following. In particular, rather than comprising a conventional valve seal 260 as illustrated in FIG. 9 to FIG. 11, the dispense interface illustrated in FIG. 12 and FIG. 14 to FIG. 16 provides an alternative flow regulation means in the form of capillary fluid channels. However, the observations regarding the features other than the valve seal 260 of the dispense interface described with reference to FIG. 1 to FIG. 11 also apply mutatis mutandis to the dispense interface according to the invention and shown in FIG. 12 and FIG. 14 to FIG. 16.

Before returning to FIG. 12 and FIG. 14 to FIG. 16, the capillary effect already described shall be explained further with reference to FIG. 13a and FIG. 13b as follows: The volume of a fluid channel is determined by the product of its cross-sectional area and its length. In the context of the following explanation, a fluid channel is said to be wide when it has a large cross-sectional area and narrow, when it has a small cross-sectional area.

Figure 13A:
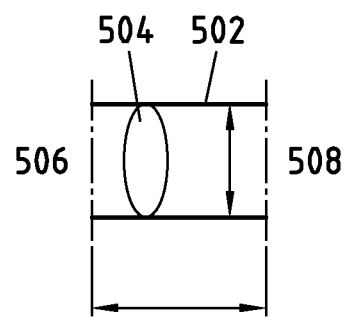
FIG. 13a-b illustrate the principle underlying the capillary effect with regard to the diffusion rate of two fluids.

FIG. 13a illustrates a first fluid channel 502 which is wide, i.e. has a large cross-sectional area 504, and short. The first fluid channel 502 connects a first fluid 506 and a second fluid 508. The total volume of the first fluid channel 502 is V.

Figure 13B:
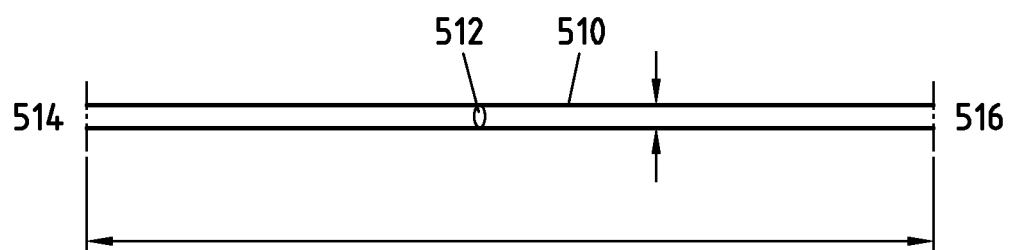

FIG. 13b illustrates a second fluid channel 510 which is narrow, i.e. has a small cross-sectional area 512, and long. The second fluid channel connects a third fluid 514 and a fourth fluid 516. The total volume of the second fluid channel 510 is also V and therefore identical to that of the first fluid channel 502.

Despite the first and the second fluids 506, 508 and the third and the fourth fluids 514, 516 being connected by a respective fluid channel 502, 510 with the identical volume V, the diffusion rate across each fluid channel 502, 510 is different.

The first fluid channel 502 which is wide and short exhibits a high concentration gradient between the first fluid 506 and the second fluid 508, which in turn results in a correspondingly high diffusion rate. The large cross-sectional area 504 permits diffusion to occur over a larger interface between the fluids 506, 508. Further, the wide form allows convection currents that also promote mixing of the first fluid 506 and the second fluid 508.

On the other hand, the second fluid channel 510 which is narrow and long, and therefore has a capillary form, exhibits a low concentration gradient. Its cross-sectional area 512 is small, resulting in diffusion occurring over a very small interface between the fluids 514, 516. The narrowness of the second fluid channel 510 also results in a low Rayleigh number that prevents convection currents from forming. Consequently the second fluid channel 510 which is narrow and long will have—despite its identical volume—a significantly lower mass transport rate than the first fluid channel 502 which is wide and short. This phenomenon forms the basis for the capillary effect.

Returning now to FIG. 12, the dispense interface 402 is mounted to the distal end 15 of the main body 14 as shown in FIG. 1, and a dose dispenser (e.g., a needle assembly) is attached to the needle hub 412 on the distal end of the dispense interface 402. This corresponds to the arrangement of the dispense interface 200 illustrated in FIG. 9.

The dispense interface 402 comprises a first cartridge stub 422 and a second cartridge stub 424, each configured to receive a respective cartridge of the cartridge holder 40 when the dispense interface 402 is connected to the distal end of the cartridge holder 40. The first and second cartridge stubs 422, 424 comprise a first and second contact protrusion 418, 420, respectively. Each contact protrusion comprises a central bore which connects to a first fluid inlet opening 414 and a second fluid inlet opening 416, respectively. The fluid from a cartridge received by either one of the cartridge stubs 422, 424 may flow into the associated fluid inlet 414, 416 opening via a needle which is arranged to permit fluid flow from a respective cartridge, for example. In particular, the needle may pierce the septum of the respective cartridge and thus be inserted into the volume of the cartridge containing the fluid.

The first fluid inlet opening 414 connects to a first capillary fluid channel 404, which is arranged in a meandering pattern on a plane perpendicular to the longitudinal axis of the dispense interface 402. In an example embodiment, the first capillary fluid channel 404 has a rounded cross-section. In another example embodiment, the first capillary fluid channel 404 has a rectangular cross-section, or a rectangular cross section in which one or more of the corners are rounded. The first capillary fluid channel 404 runs in straight and gently curved sections but without sharp turns, sharp corners or edges.

Likewise, the second fluid inlet opening 416 connects to a second capillary fluid channel 406, which is also arranged in a meandering pattern on the same plane as the first capillary fluid channel 404 and likewise runs in straight and curved sections without sharp radii or sharp corners. By avoiding sharp corners and edges, turbulences in the fluid flow, which could cause radial mixing within the capillary channels is reduced or minimised. The cross section of the second capillary fluid channel 406 may be the same or similar to that of the first capillary fluid channel 404. A rectangular cross section or a rectangular cross section with rounded corners may be easier to produce. Both the first capillary fluid channel 404 and the second capillary fluid channel 406 present a two-ended flow regulation structure in the meaning of the invention.

Both capillary fluid channels 404, 406 meet at a confluence 408, thereby combining the flow path of both capillary fluid channels 404, 406. The confluence provides a fluid outlet to a holding chamber 410. The holding chamber 410 may extend in a longitudinal direction of the dispense interface 402 and terminates in an opening at the distal end of the dispense interface 402, for example to receive an injection needle through the opening. This opening presents an outlet port in the meaning of the invention. By this arrangement of the capillary fluid channels 404, 406 and the confluence 408, the volume of the holding chamber 410, which presents the post-mix volume to be traversed by both medicaments, is minimized.

The holding chamber 410 is arranged in a needle hub 412 of the dispense interface 402. This needle hub 412 is configured to allow a dose dispenser, such as a conventional pen type injection needle assembly, to be removably mounted to the drug delivery device. Fluid from within the holding chamber 410 can then flow to that dose dispenser.

A first cartridge 90 with a primary medicament 92, e.g. insulin glargine, is connected to the first cartridge stub 422 and a second cartridge 100 with a secondary medicament 102, e.g. a GLP-1 type medicament, is connected to the second cartridge stub 424 by attaching the dispense interface 402 to the cartridge holder 40. The dispense interface 402 and the cartridge holder 40 may be configured mechanically to only allow a mutual attachment in which the first cartridge is received by the first cartridge stub 422 and the second cartridge is received by the second cartridge stub 424.

Figure 14:
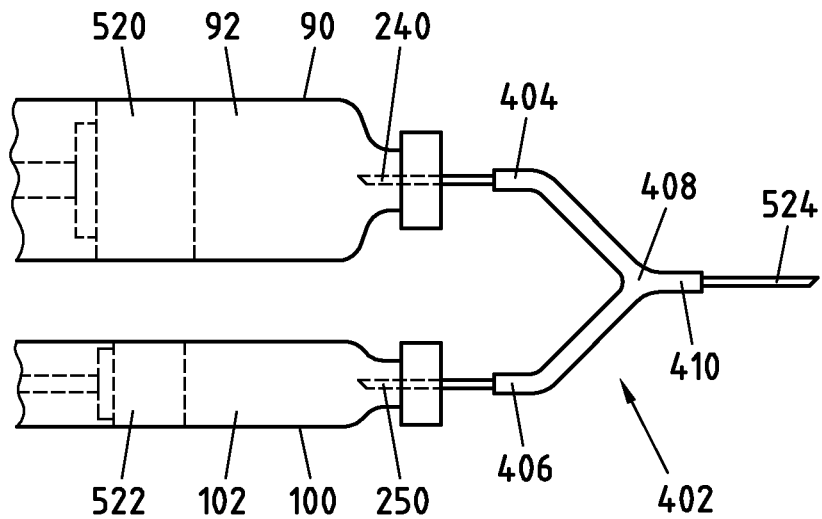
FIG. 14 illustrates an overview of the flow paths in a drug delivery device with a dispense interface according to the invention.

For an overview of the entire flow path in the drug delivery device as just described, reference is made to FIG. 14. The first cartridge 90 and the second cartridge 100 present a first reservoir and a second reservoir in the meaning of the invention. Likewise, the primary medicament 92 and the secondary medicament 102 present a first drug agent and a second drug agent in the meaning of the invention.

A first bung 520 is arranged within the first cartridge 90 and configured to apply pressure to the primary medicament 92 when it is pushed forward by a piston rod. Likewise, a second bung 522 is arranged within the second cartridge 100 and equally configured to apply pressure to the secondary medicament 102 when it is pushed forward by a piston rod.

By advancing the bungs 520, 522, the first and second medicaments 92, 102 are pushed through a first piercing needle 240 and a second piercing needle 250, respectively, and further into the first and second capillary fluid channels 404, 406.

Thereby the primary medicament 92 flows through the first piercing needle 240 further via the first capillary fluid channel 404 to the confluence 408, just as the secondary medicament 102 flows through the second piercing needle 250 further via the second capillary fluid channel 406 also to the confluence 408.

At this point, the flow path of both medicaments 92, 102 merges and finally leads through the holding chamber 410 to the outlet needle 524. This illustrates firstly that each medicament has a dedicated flow path (the flow path up until the confluence 408) and a flow path that is shared with the other medicaments, namely from the confluence 408 to the injection needle 524. Secondly, it illustrates that there is also a theoretical flow path from the first cartridge 90 to the second cartridge 100 and vice versa.

The diameter for the first and second capillary fluid channel 404, 406 is 0.3 mm. The total volume of the first capillary fluid channel 404, which is known to conduct the primary medicament, may amount to 50 microliters. The total volume of the second capillary fluid channel 406, which in turn is known to conduct the secondary medicament, may amount to 30 microliters due to differences between the compliances of the first and second cartridges.

The exact sequence, respective timing and volume of injection of all fluids to be injected may be determined in any number of ways for a particular use case. In general, the dispense interface according to the invention is most effective when a dispense sequence of the medicaments from the cartridges is utilized which minimizes mutual contamination of any capillary fluid channel with medicaments that are flowing back from another cartridge. For example, even if there is limited backflow into a capillary fluid channel, any medicament that has flowed back in this way can be flushed out by a subsequent discharge of the medicament associated with the capillary fluid channel into which the backflow has occurred. In this way, the medicament being discharged will push the medicament that has flowed back such that it moves toward the injection needle.

As an example, it may be determined that a prescribed volume of injection of the primary medicament is followed in time by a further prescribed volume of injection of the secondary medicament.

Prior to any cartridge being discharged through the application of pressure, neither fluid from the first cartridge nor fluid from the second cartridge diffuses through the first capillary fluid channel 404 or the second capillary fluid channel 406. That is because the length, cross-sectional area and total volume of each capillary fluid channel 404, 406 is chosen so as to effect a diffusion time of about a year for each.

In general, the rate of diffusion depends on temperature and molecular weight of the medicament or medicaments. The molecular weight may be relatively high for certain medicaments, thereby providing a relatively low rate of diffusion to begin with. By restricting the diameter of a fluid channel, convection currents in the fluid channel are reduced or eliminated, thereby further reducing the rate of mass transport and, as a corollary, increasing the transport time. To determine if and how much convection occurs, the relevant Rayleigh number as a function of the properties of the capillary fluid channel 404, 406 and the properties of the appropriate fluid can be determined.

Thereby, both capillary fluid channels 404, 406 have a similar or even superior effect as a conventional membrane valve in preventing cross-contamination of the fluid contents of the cartridges.

As an initialization of the capillary channel structure, each capillary fluid channel may be primed by being pre-filled with its respective medicament. A prerequisite for this is that the injection needle must be fitted. For this priming, a pre-filling pressure is applied to the primary and secondary medicament which causes an advancement flow of each medicament through its respective capillary fluid channel 404, 406, to the confluence 408, the holding chamber 410 and further all the way to the injection needle 524.

Advancements of the respective medicament flow during this priming are preferably in the ratio of cartridge compliances so that there is no back-flow into either capillary fluid channel. In particular, the pre-filling pressure is preferably applied to each medicament either simultaneously or, as an alternative, incrementally and in an interleaved fashion. Thereby the respective pressure in each cartridge is substantially equal at all times during priming. Advancements are preferably also made slowly so that, unless there is a blockage in the needle, the developed pressures are low.

Consequently, in the case that a needle is fitted and there is no blockage, both capillary fluid channels 404, 406, the confluence 408, the holding chamber 410 and the outlet needle are filled with the corresponding one of the medicaments 92, 102 and thereby primed. If, on the other hand, there is a blockage in the needle or in the holding chamber 410 during priming, the described manner of advancing the flow, i.e. simultaneously or interleaved, ensures that there is no reverse flow from one capillary fluid channel to the other. Thus, contamination is avoided.

As the ejection proceeds, the first medicament is ejected. Pressure applied to the primary medicament in the first cartridge causes the primary medicament to flow through the first capillary fluid channel 404 via the confluence 408 to the holding chamber 410 and further into the injection needle.

Optionally, during the ejection of the primary medicament, a biasing pressure is applied to the secondary medicament in the second capillary fluid channel 406. This biasing pressure may cause no or very little movement of the secondary medicament through the second capillary fluid channel 406 into the confluence 408. However, the biasing pressure suffices to prevent reverse flow of the primary medicament into the second capillary fluid channel 406.

In a desired delivery schedule in which the secondary medicament is to be injected first, the biasing pressure as just described may be applied to the first medicament in the first capillary fluid channel 404.

After the ejection of the primary medicament is complete, pressure is applied to the secondary medicament in the second cartridge, causing the secondary medicament to flow through the second capillary fluid channel 406 via the confluence 408 to the holding chamber 410 and also into the injection needle. Any primary medicament which may have flowed in the reverse direction into the second capillary fluid channel 406 from the confluence 408 is also pushed out of the second capillary fluid channel 406 into the injection needle by the secondary medicament, thereby ensuring that this amount of the primary medicament is injected as well.

Any primary medicament remaining in the first capillary fluid channel 404 prevents any secondary medicament from flowing into the first capillary fluid channel 404 in a reverse direction.

For a different situation and for different medicaments, the injection sequence between primary and secondary medicament may be reversed.

Yet even for the case that no biasing pressure as just described is applied to the medicaments in the cartridge that is not currently delivered, i.e. pressure is only applied to the specific medicament to be delivered, backflow may be prevented by structural arrangements.

Figure 15:
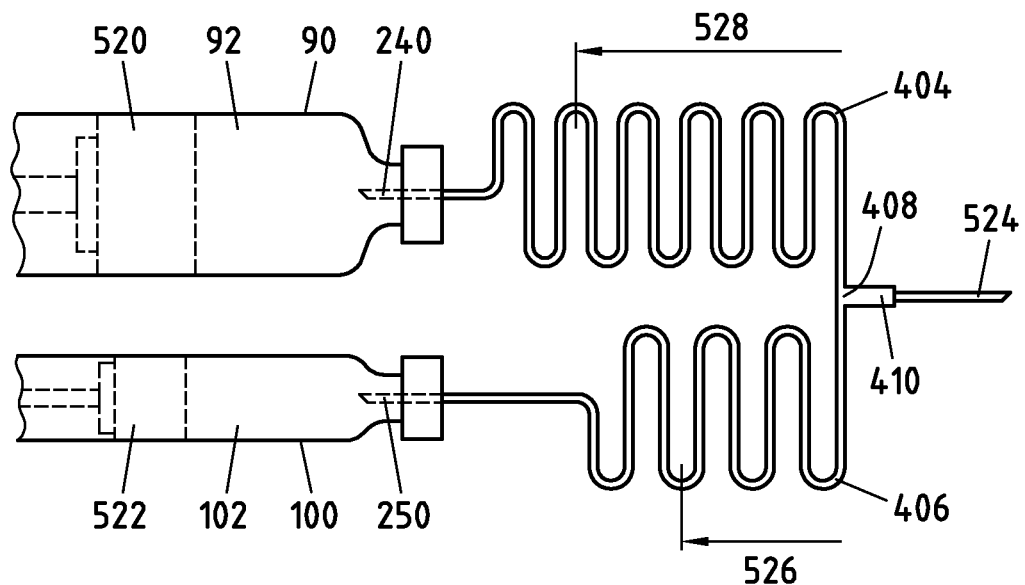
FIG. 15 illustrates containment of the backflow of drug agents within capillary fluid channels of a dispense interface according to the invention.

In particular, when little or no biasing pressure is applied to the secondary medicament in the second capillary fluid channel 406 during the time that pressure is applied to the primary medicament during its delivery, contamination of the secondary medicament 102 within the second cartridge 100 is avoided by the volume of the second capillary fluid channel 406. This effect is illustrated in FIG. 15, which shows the same arrangement as illustrated in FIG. 14 with a more detailed view of the capillary fluid channels 404, 406.

When the primary medicament 92 is to be delivered, it is being pushed out of the first cartridge 90 by the first bung 520. Since no pressure is applied to the secondary medicament 100 at this point, in the case of a pressure drop in the injection needle 524 or a blockage, e.g. in the holding chamber 410, backflow of the primary medicament 92 into the second capillary fluid channel 406 can occur. However, the volume of the second capillary fluid channel 406 is chosen such that even in the case of backflow the primary medicament will only flow up to the first backflow point 526 in the second capillary fluid channel 406. Thus, no contamination of the secondary medicament 102 in the second cartridge 100 occurs. When the secondary medicament 102 is subsequently pushed out of its cartridge 100, the primary medicament 92 which has flowed back until the first backflow point 526 is flushed out by the secondary medicament 102.

The analogous situation occurs when the secondary medicament 102 is to be delivered first. In that case, it is being pushed out of the second cartridge 100 by the second bung 522. Since no pressure is applied to the primary medicament 92 at this point, in the case of a pressure drop in the injection needle 524 or a blockage, e.g. in the holding chamber 410, backflow of the secondary medicament 102 into the first capillary fluid channel 404 can occur. However, the volume of the first capillary fluid channel 404 is chosen such that even in the case of backflow the secondary medicament 102 will only flow up to the second backflow point 528 in the first capillary fluid channel 404. Thus, no contamination of the primary medicament 92 in the second cartridge 90 occurs. When the primary medicament 92 is subsequently pushed out of its cartridge 90, the secondary medicament 102 which has flowed back until the second backflow point 528 is flushed out by the primary medicament 92.

Thereby the volume of the first and second capillary fluid channels 404, 406 is used as a containment volume for absorbing potential backflow. In order to achieve a sufficient volume of the capillary fluid channel that is to be used for such a containment of the backflow without having a very long length of that capillary fluid channel, a diameter of the capillary fluid channel of around 0.3 mm is preferred.

Choosing a smaller diameter, for example a diameter of 0.1 mm, results in a very narrow but long channel that may cause a large pressure drop along the length of the channel, which may be disadvantageous.

It is pointed out that beside the capillary fluid channels 404, 406, there are also the first and second piercing needles 240, 250 which can be taken into account for, on the one hand, preventing undesired diffusion and convection currents from the cartridges 90, 100, and also, on the other hand, for absorbing potential backflow in the same way as was just described for the capillary fluid channels 404, 406.

Because the first and second piercing needles 240, 250 have a narrow bore with a cross-sectional area that may be even smaller than that of the capillary fluid channels 404, 406 and a typical length of only 15 mm, the volume of the first and second piercing needles 240, 250 by itself may be extremely small and so insufficient to fully contain backflow. However, the volume of the piercing needles 240, 250 may be taken into account when the capillary fluid channels 404, 406 are dimensioned for containment of the backflow. In other words, implementing such a 'mixed strategy' relying both on the capillary fluid channels 404, 406 and the piercing needles 240, 250 may allow for a smaller required volume on the part of the capillary fluid channels compared to the situation in which the volume of the piercing needles 240, 250 is not accounted for.

Also, because the first and second piercing needles 240, 250 have a narrow bore with a cross-sectional area that may be even smaller than that of the capillary fluid channels 404, 406, then relying both on the capillary fluid channels 404, 406 and the piercing needles 240, 250 may allow for an improved capillary barrier compared to the situation in which the capillary effect of the piercing needles 240, 250 is not accounted for.

As a different example, a situation is now considered in which it is determined that a prescribed volume of injection of the primary medicament is injected at the same time as a second prescribed volume of injection of the secondary medicament. That means that pressure sufficient for delivering the medicaments is applied substantially simultaneously to the first medicament and the second medicament.

Thereby also in this scenario and as described above for the priming process, advancements of the respective medicament flow during this prime are preferably in the ratio of cartridge compliances so that there is no back-flow into either capillary fluid channel. The pressure for delivering the medicaments is preferably applied to each medicament either simultaneously or, as an alternative, incrementally and in an interleaved fashion in the same way. Thereby also here the respective pressure in each cartridge is substantially equal at all times during delivery of the medicaments and backflow is prevented. In those instances where the capillary fluid channels have very small diameters and long lengths, there may be substantial pressure drops in the capillary fluid channels during delivery. Such substantial pressure drops must be considered when calculating the pressures to be applied to the medicaments, as may be determined by hydraulic flow considerations by those skilled in the art.

The dispense interface 402 illustrated in FIG. 12 may be manufactured by assembling two constituent integral parts, in particular by assembling a distal integral part and a proximal integral part. Both constituent parts are made of polyolefin or cyclopolyolefin and therefore do not have any elastomeric elements. Both constituent parts may be manufactured using conventional moulding technology.

Figure 16:
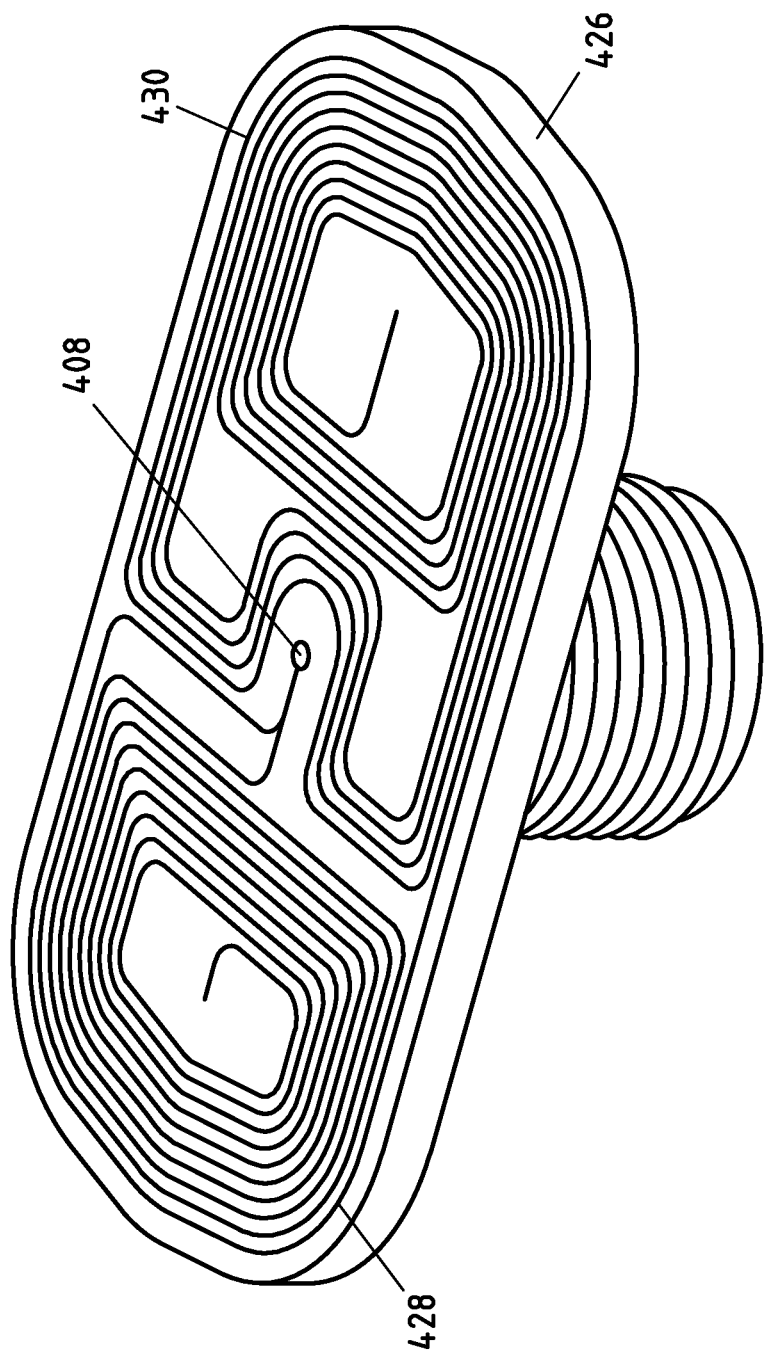
FIG. 16 illustrates a perspective view of a distal integral part of the dispense interface according to the invention illustrated in FIG. 12.

FIG. 16 illustrates a distal integral part 426 which is a constituent integral part of the dispense interface 402 illustrated in FIG. 12. The distal integral part 426 comprises the needle hub 412 and the confluence 408. Further, the top surface of the distal integral part 426 provides the first lower wall boundary 430 of the first capillary fluid channel 404 and the second lower wall boundary 428 of the second capillary fluid channel 406. The first lower wall boundary 430 and the second lower wall boundary 428 present a second boundary surface in the meaning of the invention. By joining the distal integral part 426 with its proximal counterpart and the lower wall boundaries 428, 430 with their upper wall boundary counterparts on the proximal integral part, the first and second capillary fluid channels 404, 406 are formed. This way of manufacturing the capillary fluid channels 404, 406 is more economical than drilling or otherwise creating a hole or bore with the dimensions of the capillary fluid channels 404, 406.

The distal integral part 426 and the proximal integral part may be joined by laser welding, ultrasonic welding, diffusion bonding or by adhesive bonding.

The dispense interface 402 further accommodates bung compression effects which may arise when the needle is blocked, i.e. it is not damaged when such a block occurs. This also applies to smaller tidal volume effects that occur for example due to small temperature changes that are experienced by the device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptaωdecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface for a drug delivery device for delivering at least two drug agents, comprising:
   at least two flow regulation structures configured to connect to at least two fluid reservoirs; and
   a confluence at which the at least two flow regulation structures meet,
   wherein each flow regulation structure has a first end and a second end and comprises:
      a fluid inlet opening at the first end, the fluid inlet opening of each flow regulation structure configured to connect to a different one of the at least two fluid reservoirs, and
      a fluid outlet opening at the second end connected to the confluence,
   wherein one or more of the at least two flow regulation structures each further comprises a capillary fluid channel that ends at the confluence,
      each capillary fluid channel having a volume configured to contain a backflow from one or more others of the at least two flow regulation structures, and arranged in a meandering pattern on a plane perpendicular to a direction of fluid flow through an outlet of the confluence.

2. The dispense interface of claim 1, wherein each of the at least two flow regulation structures comprises a respective capillary fluid channel that ends at the confluence.

3. The dispense interface of claim 1, wherein at least one of the at least two flow regulation structures further comprises a valve.

4. The dispense interface of claim 3, wherein at least one of the at least two flow regulation structures comprises a sequential arrangement of the valve and the capillary fluid channel that ends at the confluence.

5. The dispense interface of claim 1, wherein the confluence is configured to permit flow to a holding chamber of the dispense interface.

6. The dispense interface of claim 1, wherein each of the at least two fluid reservoirs is in the form of a respective fluid cartridge, and wherein the dispense interface further comprises a stub around each fluid inlet opening at the first end of each flow regulation structure, wherein each stub is configured to receive a different one of the at least two fluid cartridges.

7. The dispense interface of claim 1, formed from at least two integral parts including:
   a first integral part comprising a proximal end of the dispense interface; and
   a second integral part comprising a distal end of the dispense interface.

8. The dispense interface of claim 7,
   wherein the first integral part comprises a first boundary surface of each capillary fluid channel and
   wherein the second integral part comprises a second boundary surface of each capillary fluid channel.

9. The dispense interface of claim 7, wherein each capillary fluid channel is formed by a joining of the first integral part and the second integral part.

10. A drug delivery device for delivering at least two drug agents comprising a dispense interface according to claim 1.

11. The dispense interface of claim 2, wherein a first volume of a first capillary fluid channel of a first of the at least two flow regulation structures is less than a second volume of a second capillary fluid channel of a second of the at least two flow regulation structures.

12. The dispense interface of claim 1, further comprising a holding chamber extending in a longitudinal direction of the dispense interface and configured to receive a fluid flow from the outlet of the confluence.

* * * * *